(12) United States Patent
Yamauchi et al.

(10) Patent No.: US 8,993,715 B2
(45) Date of Patent: Mar. 31, 2015

(54) LABELED PROTEIN AND METHOD FOR OBTAINING THE SAME

(75) Inventors: Fumio Yamauchi, Yokohama (JP);
Satoshi Ogawa, Tokyo (JP); Kengo Kanazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 626 days.

(21) Appl. No.: 12/830,244

(22) Filed: Jul. 2, 2010

(65) Prior Publication Data
US 2011/0009601 A1 Jan. 13, 2011

(30) Foreign Application Priority Data

Jul. 6, 2009 (JP) .................. 2009-159859

(51) Int. Cl.
*C07K 7/00* (2006.01)
*C07K 1/13* (2006.01)
*C07K 16/32* (2006.01)

(52) U.S. Cl.
CPC . *C07K 1/13* (2013.01); *C07K 16/32* (2013.01); *C07K 2317/622* (2013.01); *C07K 2319/21* (2013.01); *C07K 2319/31* (2013.01)
USPC .......................................... 530/300; 530/350

(58) Field of Classification Search
None
See application file for complete search history.

(56) References Cited

U.S. PATENT DOCUMENTS

| 5,876,691 A * | 3/1999 | Chester et al. ............... 424/1.49 |
| 7,368,254 B2 * | 5/2008 | Jorgensen et al. ............ 435/7.23 |
| 2005/0069962 A1 * | 3/2005 | Archer et al. .................. 435/7.9 |
| 2008/0118562 A1 * | 5/2008 | Koya ............................ 424/486 |
| 2010/0256301 A1 * | 10/2010 | Cebolla Ramirez et al. 525/54.1 |

FOREIGN PATENT DOCUMENTS

| JP | H02-002937 A | 1/1990 |
| JP | H09-325142 A | 12/1997 |
| WO | 2004096989 A2 | 11/2004 |
| WO | 2006008096 A1 | 1/2006 |
| WO | 2007047342 A1 | 4/2007 |
| WO | 2009/000784 | * 12/2008 |
| WO | 2009020093 A1 | 2/2009 |
| WO | 2009/034204 | * 3/2009 |

* cited by examiner

*Primary Examiner* — Sheela J Huff
(74) *Attorney, Agent, or Firm* — Canon U.S.A. Inc., IP Division

(57) ABSTRACT

It is an object of the present invention to obtain a labeled protein, and specifically, to separate a labeled protein and the same unlabeled protein. There is provided a labeled protein including: a protein to be labeled having a target protein, at least one or more affinity interaction domains for binding to an affinity support, and at least one or more labeling sites; and a labeling reagent binding to at least one of the labeling sites; wherein the affinity of the labeled protein for the affinity support is difference from that of the protein to be labeled for the affinity support.

5 Claims, 3 Drawing Sheets

LABELED PROTEIN AND METHOD FOR OBTAINING THE SAME

BACKGROUND OF THE INVENTION

1. Field of the Invention

The present invention relates to a labeled protein for obtaining the labeled protein in high purity and a method for obtaining the same. More specifically, the invention relates to a labeled antibody useful for diagnostic application and a purification method thereof.

2. Description of the Related Art

A labeled protein including a labeled antibody is used for diagnosis of lesions such as cancer. The labeled protein includes a protein binding to a molecule specifically present in a lesion part, and as a labeling substance, a signal-generating part which enables detection from the outside of the living organism or a chemical modifier which modifies physical and chemical properties of the protein. Since the labeled protein binds to the specific molecule and the labeling substance sends a signal, the detection of the signal enables the present/absence of the specific molecule and the amount and location information thereof to be obtained.

Upon using the labeled protein as a diagnosis agent or a contrast agent, an unlabeled protein mixed therewith causes competitive inhibition and thereby decreases the detection sensitivity. Therefore, a method for separating and purifying a labeled protein is desired.

However, it is difficult to separate a labeled protein and an unlabeled protein after labeling. In particular, when a low molecular compound such as fluorescent dye and water-soluble oligo (ethylene glycol) is used as a labeling reagent, the separation becomes further difficult. This is because labeling with a low molecular compound does not make a large difference between the labeled substances before and after labeling in the physical and chemical properties (a molecular size, hydrophilicity/hydrophobicity, an electric charge, etc.).

Size exclusion chromatography, ion-exchange chromatography and hydrophobic chromatography can be used to separate a labeled protein. However, in the case of labeling with a low molecular compound, it is not easy to separate a labeled protein and an unlabeled protein even with these chromatography methods, and detailed investigation of conditions is necessary. In stead of size exclusion chromatography, an antibody against a labeling reagent can be used for separation of a labeled protein. However, this method is not versatile because the antibody is not always available.

As a method for purifying a labeled protein, a method for separating a labeled protein from an unlabeled protein using hydrophobic chromatography (Japanese Patent Application Laid-Open No. H09-325142, separation purification method with a hydroxyapatite column (Japanese Patent Application Laid-Open No. H02-002937) are reported.

SUMMARY OF THE INVENTION

A protein to be purified may be denatured by the method disclosed in Japanese Patent Application Laid-Open No. H09-325142.

It has been considered that separation by hydroxyapatite column uses ion exchange or electrostatic force between the protein to be separated and the carrier. Therefore, separation with hydroxyapatite column has the following problems. (i) Optimal condition for each protein is different. Therefore, the optimal condition including pH of solvent, salt concentration, flowing rate have to be searched for each of the proteins. (ii) There is a fear that the protein may be denatured when absorbing to hydroxyapatite. (iii) Proteins having similar surface condition (such as electric potential on the surface or hydrophilicity/hydrophobicity) cannot be separated.

It is an object of the present invention to obtain a labeled protein, and especially, to separate a labeled protein and the same unlabeled protein.

The inventor carried out earnest investigation of a method for obtaining a labeled protein to achieve the solution of the aforementioned problem and completed the present invention.

In other words, a first aspect of the present invention is to provide a labeled protein including: a protein to be labeled having a target protein, at least one or more affinity interaction domains for binding to an affinity support, and at least one or more labeling sites; and a labeling reagent binding to at least one of the labeling sites; wherein the affinity of the labeled protein for the affinity support is different from that of the protein to be labeled for the affinity support.

Furthermore, a second aspect of the present invention is to provide a labeled protein represented by formula (1):

$$Z\text{-}(L)_a\text{-}X\text{-}Y) \tag{1}$$

wherein, Z represents a target protein; L may or may not represent a linker amino acid; X represents a polypeptide having a labeling site and an affinity interaction domain for binding to an affinity support; Y represents a labeling reagent binding to the labeling site; and a is 0 or 1, and wherein the affinity of a protein to be labeled, which corresponds to the formula (1) lacking Y, for the affinity support is different from that of the labeled protein represented by the formula (1) for the affinity support.)

Moreover, a third aspect of the present invention is a method for obtaining a labeled protein, including: i) providing a protein to be labeled having a target protein, an affinity interaction domain and a labeling site; ii) connecting a labeling reagent to the labeling site of the protein to be labeled to obtain the labeled protein binding to the labeling reagent; iii) bringing into a mixture of the labeled protein and the protein to be labeled without the labeling reagent contact with an affinity support capable of binding specifically to the affinity interaction domain; and iv) selecting the labeled protein based on the difference between the affinities for the affinity support.

Affinity purification enables separation of the labeled protein of the present invention from the same unlabeled protein and easy purification of the labeled protein.

Herein after, why the protein of the present is superior to purification using conventional columns or hydroxyapatite column will be explained more in detail. The protein of the present invention can be simply separated only by one step because the labeled proteins are collected as through out, while general method using column requires at least two steps (binding step and elution step). Further, the protein does not denature because the labeled protein of the present invention is collected without binding to the carrier. Even in case that they weekly bind to the carrier, they hardly denature because they bind to the carrier via affinity interaction domain and not via the target protein. Furthermore, the present invention can be applied for various target proteins.

Further features of the present invention will become apparent from the following description of exemplary embodiments with reference to the attached drawings.

DESCRIPTION OF THE EMBODIMENTS

Figure 1A:
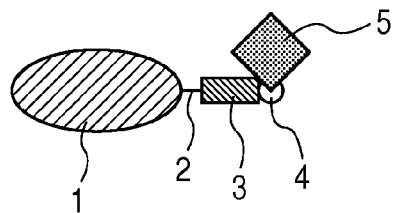
FIGS. 1A, 1B, 1C and 1D are schematic diagrams illustrating a labeled protein according to the embodiment of the present invention.
Figure 1B:
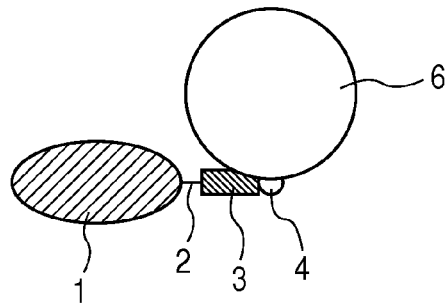
Figure 1C:
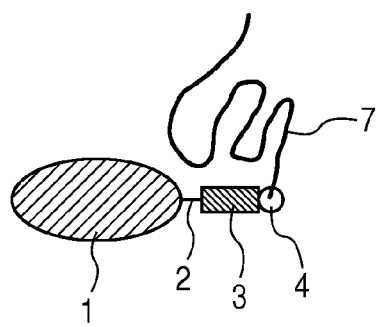
Figure 1D:
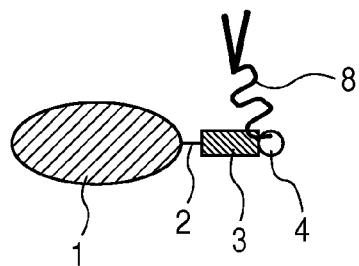

Preferred embodiments of the present invention will now be described in detail in accordance with the accompanying drawings.

The labeled protein according to the embodiment of the present invention will be described in detail below.

The invention is a labeled protein including a protein to be labeled and a labeling reagent. The protein to be labeled has a target protein, at least one or more affinity interaction domains for binding to an affinity support, and at least one or more labeling sites. The labeling reagent binds to at least one of the labeling sites. The affinity of the labeled protein for the affinity support is different from that of the protein to be labeled for the affinity support.

One example of the labeled protein according to the present invention includes a labeled protein represented by formula (1):

$$Z-(L)_a-X-Y \quad (1)$$

wherein, Z represents a target protein; L represents a linker amino acid including a polypeptide; X represents a polypeptide having a labeling site and an affinity interaction domain for binding to an affinity support; Y represents a labeling reagent binding to the labeling site; and a is 0 or 1, and wherein the affinity of a protein to be labeled, which does not bind to Y in the formula (1)), for the affinity support is different from that of the labeled protein represented by the formula (1) for the affinity support.)

The difference between the affinities of the labeled protein and the protein to be labeled for the affinity support enables the separation and purification of the labeled protein from the protein to be labeled.

The labeled protein of the embodiment of the present invention is represented by FIGS. 1A to 1D. The examples of FIG. 1A, FIG. 1B, FIG. 1C, and FIG. 1D use, as a labeling reagent, dye, a particle, PEG, a pegylated phospholipid, respectively. In addition, 1 represents a target protein; 2 represents a linker amino acid; 3 represents an affinity interaction domain; 4 represents a labeling site; 5 represents dye; 6 represents a particle; 7 represents a PEG; and 8 represents a pegylated phospholipid.

Target Protein

In the embodiment, target protein 1 means a protein intended to be labeled. The target protein is not particularly limited, and includes, for example, an enzyme, an antibody, an antibody fragment, a receptor, a cytokine, a hormone and a serum protein and particularly preferable examples include an antibody and an antibody fragment. The antibody is a general term indicating an immunoglobulin family protein which is induced by an immune system in response to a specific antigen or substance, and can recognize a specific molecule and bind to the molecule. The antibody and the antibody fragment may be derived from any animals such as a human, a mouse, a rat, a camel and a bird, and further may be derived from a chimera. The antibody may be a polyclonal antibody or a monoclonal antibody. The antibody fragment means a derivative of a low molecular antibody maintaining its binding capacity to a target molecule. The antibody fragment includes an Fab fragment, an Fab' fragment, an F(ab')$_2$, a variable heavy-chain (VH) domain alone, a variable light-chain (VL) domain alone, a VH-VL complex, and a peptide containing a camel VH domain or a complementarity determining region (CDR) of an antibody. Among these, particularly preferably, a single chain antibody (scFv) in which a variable heavy-chain domain is connected to a variable light-chain domain via a peptide linker can be used. Particularly more preferably, a human single chain antibody (scFv) can be used. Since the antibody fragment has smaller molecular size as compared with the antibody, and thereby has high tissue permeability and high clearance rate, its application to a diagnosis agent or a contrast agent is promising. A desirable antibody or antibody fragment of these, particularly, connects to a molecule which expresses in lesion sites at high level. Examples of the molecule which expresses in lesion sites at high level may include, for example, receptor tyrosine kinase HER2 and carcinoembryonic antigen (CEA). HER2 gene is a cancer-associated gene, and its gene amplification can be found in many cancer types. CEA is a glycoprotein and strongly expresses in adenocarcinomas of endodermally-derived digestive system epithelia as well as in breast cancer and non-small-cell lung cancer.

Examples of the above-mentioned target protein include the polypeptide having the amino acid sequence described below:

(SEQ ID NO: 38)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASG

FNIKDTYIHWVRQAPGKGLEWVARIYPTNGYTRYADSVKGRFTISADTSK

NTAYLQMNSLRAEDTAVYYCSRWGGDGFYAMDYWGQGTLVTVSS.

Further, the above-mentioned target protein preferably includes the polypeptide having the amino acid sequence described below.

(SEQ ID NO: 21)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASG

FNIKDTYIHWVRQAPGKGLEWVARIYPTNGYTRYADSVKGRFTISADTSK

NTAYLQMNSLRAEDTAVYYCSRWGGDGFYAMDYWGQGTLVTVSSAAALE

HHHHHGGC

Affinity Interaction Domain

In the embodiment, an affinity interaction domain means a domain which has one of two or more substances having an affinity specific to each other or a partial structure thereof. Known examples of the two or more substances having an affinity specific to each other are an antigen and antibody, an enzyme and enzyme substrate, a receptor and ligand such as a hormone, a chelated metal ion and trapping substance thereof, nucleic acids (DNA, RNA) and the complementary binds thereof, and biotin and avidin. An affinity support means a support which has an affinity specific to the affinity interaction domain and is used for immobilization and purification of a molecule containing the affinity interaction domain. Examples of the affinity support include a dextran or agarose having one of the two or more substances having an affinity specific to each other immobilized thereon. The affinity support can be used for affinity purification, in which a substance having the affinity interaction domain is separated and purified by developing a solution of the substance to be separated on the support.

In the embodiment, the affinity interaction domain can be any substance which can interact and is not particularly limited. Examples of the affinity interaction domain include an oligo-histidine peptide with at least 4 or more histidines, a maltose-binding peptide (MBP), an albumin-binding peptide (ABP), a peptide containing biotin. When the affinity interaction domain is a maltose-binding peptide (MBP), maltose or an anti-MBP antibody can be used as the affinity support; when the affinity interaction domain is an oligo-histidine peptide with at least 4 or more continuous histidine, a nickel complex compound connected to nitrilotriacetic acid (Ni-NTA) or an anti-oligo-histidine antibody can be used as an affinity support; when the affinity interaction domain is an albumin-binding peptide (ABP), albumin or an anti-albumin antibody can be used as the affinity support; when the affinity interaction domain is a peptide containing biotin, avidin or an avidin derivative, or an anti-biotin antibody can be used as the affinity support.

As the affinity interaction domain, oligo-histidine peptides, particularly, a hexapeptide His-His-His-His-His-His can be preferable because its affinity interaction domain itself is so small that the function of a target protein is not inhibited. An oligo-histidine connects to a divalent metal ion such as $Cu^{2+}$, $Zn^{2+}$, $Ni^{2+}$, $Co^{2+}$, $Mg^{2+}$, and particularly, connects to $Ni^{2+}$ ion. It is known that an oligo-histidine peptide can be affinity-purified using the affinity support obtained by chelating these metals (e.g. nitrilotriacetic acid-chelated $Ni^{2+}$ or iminodiacetic acid-chelated $Ni^{2+}$).

Labeling Site

In the embodiment, a labeling site means a site for connecting a labeling reagent. The labeling site may be contained in the affinity interaction domain or the target protein. The labeling site may include, for example, an amino acid residue having an amino group, a carboxyl group, a hydroxyl group, a thiol group, a maleimide group, a hydroxysuccinimide group, an aldehyde group, an isothiocyanate group or a glycidyl group. These functional groups may be groups which an amino acid residue originally has or may be attached to an amino acid residue by chemical reaction or the like.

As a labeling site, more preferably, lysine, glutamic acid, aspartic acid, cysteine and tyrosine can be used. From the viewpoint of reaction specificity and the facility of introducing the labeling site, cysteine having a side-chain thiol group or lysine having a side-chain ε-amino group can be used more preferably. In these cases, the labeling reagent can be connected via the side-chain thiol group or the side-chain ε-amino group.

Protein to be Labeled

In the embodiment, a protein to be labeled means a protein having a target protein, at least one or more affinity interaction domains connected to an affinity support, and at least one or more labeling sites. The specification may indicate, by the protein to be labeled, the state of a protein which is not particularly labeled. In the protein to be labeled, the labeling site may be contained in the affinity interaction domain, and the protein to be labeled according to the embodiment may have, as a sequence containing both of the affinity interaction domain and the labeling site, for example, the following sequences:

```
                                                  (SEQ ID NO: 1)
His-His-His-His-His-His-Gly-Gly-Cys;

(SEQ ID NO: 2)
His-His-His-His-His-His-Cys;

(SEQ ID NO: 3)
Cys-His-His-His-His-His-His;

(SEQ ID NO: 4)
Cys-His-His-His-His-His-His-Cys;

(SEQ ID NO: 5)
Cys-His-His-His-His-His-His-Gly-Gly-Cys;

(SEQ ID NO: 6)
Ala-Ala-Ala-Leu-Glu-His-His-His-His-His-Gly-Gly-Cys;

(SEQ ID NO: 7)
Ala-Ala-Ala-Leu-Glu-His-His-His-His-His-Cys;

(SEQ ID NO: 8)
Ala-Ala-Ala-Leu-Glu-Cys-His-His-His-His-His-His;

(SEQ ID NO: 9)
Ala-Ala-Ala-Leu-Glu-Cys-His-His-His-His-His-Cys;

(SEQ ID NO: 10)
Ala-Ala-Ala-Leu-Glu-Cys-His-His-His-His-His-Gly-Gly-Cys;

(SEQ ID NO: 11)
Ala-Ala-Ala-Cys-His-His-His-His-His-His;

(SEQ ID NO: 12)
Ala-Ala-Ala-Gly-Cys-Gly-Gly-Leu-Glu-His-His-His-His-His-His;
```

-continued (SEQ ID NO: 13)
Ala-Ala-Ala-Cys-Leu-Glu-His-His-His-His-His-His;
and (SEQ ID NO: 14)
Ala-Ala-Ala-Leu-Cys-His-His-His-His-His-His.

These sequences can be bound to either N-terminus or C-terminus, unless the function of the target protein is impaired. Further, amino acid residues may be attached between the target protein and these sequences as appropriate. When the target protein is a single-chain antibody, since the sequence of its N-terminus side is deeply involved in antigen recognition, the above-mentioned sequences should be desirably attached to its C-terminus side.

Linker Amino Acid

In addition, the protein to be labeled according to the embodiment may or may not have a linker amino acid between each of the target protein, the affinity interaction domain, and the labeling site. The linker amino acid has a function of spatially separating the target protein from the affinity interaction domain or the labeling site mutually. These three should be separated in such a manner not to have a negative effect on each other in the functionality. In particular, the linker amino acid should be flexible so that the arrangement of them is not spatially overlapped. The examples of the amino acid include alanine, cysteine, aspartic acid, glutamic acid, threonine, valine, tryptophan, phenylalanine, glycine, isoleucine, leucine, methionine, asparagines, proline, glutamine, arginine, lysine, serine and tyrosine. The composition and number of the amino acid residues are not particularly limited, if the amino acid has flexibility and does not considerably decrease its water solubility. Preferably, the length can be 1 to 30 amino acids, and a linker amino acid having 1 to 15 amino acids can be particularly preferable. For example, Leu-Gly, Gly-Ala, Ser-Ala, Gly-Gly, Gly-Gly-Gly, Gly-Gly-Gly-Gly (SEQ ID NO: 15), Gly-Gly-Gly-Gly-Ser (SEQ ID NO: 16), Ala-Ala-Ala-Leu-Glu (SEQ ID NO: 17) can be suitably used from the viewpoint of flexibility. Needless to say, the linker amino acid may not be used.

In the embodiment, the protein to be labeled can be produced as a fusion protein from bacteria or cells using the recombinant DNA technique of the genetic engineering. As described below in the examples, a gene cDNA encoding the amino acid sequence of the labeling site or the affinity interaction domain is connected to a cDNA encoding the target protein at the N-terminus or C-terminus of the target protein, and thereby the protein to be labeled can be expressed in the fused state.

Alternatively, the protein to be labeled may be prepared by connecting the target protein, the affinity interaction domain and the labeling site by chemical reaction. In that case, the linker amino acid can be inserted between each of the target protein, the affinity interaction domain, and the labeling site to connect them. In any cases, the protein to be labeled is prepared under the condition in which the functions of the affinity interaction domain, the target protein and the labeling site do not have negative effects on each other. When chemical reaction connects them, the affinity interaction domain and the labeling site can be introduced via the connection with amino terminus, carboxy terminus, lysine residue or cysteine residue of the target protein, preferably, via the reaction with carboxy terminus of the target protein.

Furthermore, the protein to be labeled may be prepared by combining genetic recombination and chemical reaction. For example, after preparing the affinity interaction domain, the labeling site and the target protein individually by genetic recombination, these may be connected by chemical reaction. Alternatively, the target protein prepared by genetic recombination may be connected by chemical reaction to the affinity interaction domain or the labeling site which is chemically synthesized.

On preparing the protein to be labeled, the target protein, the affinity interaction domain, the labeling site by genetic recombination, these can be obtained by expressing a tag molecule or a fusion protein through a host or in vitro transcription. A vector is not particularly limited if it can express the protein of interest, and for example, a plasmid, a cosmid, a phagemid, and a virus vector may be used. To prepare the vector, for example, in case of expressing the protein to be labeled, after synthesizing a cDNA having a nucleotide sequence encoding the amino acid sequence of a fusion protein according to a known method, the cDNA thus obtained can be inserted to a proper vector. A vector encoding a part of oligo-histidine, which can be used as the affinity interaction domain (e.g. pET series, distributed by Novagen Inc.) is commercially available. The host is not particularly limited if the vector therein can express a peptide or a protein. For example, an animal cell, an insect cell, *E. coli* and yeasts can be included. The target protein can be obtained by culturing these hosts as appropriate after introducing the vector to the hosts according to a well-known transformation method. Further, in vitro transcription enables synthesis of a tag molecule or a protein, and commercial kits (e.g. RTS system, distributed by Roche Diagnostics) can be used for the method. In addition, a series of operation regarding the genetic recombination is not particularly limited to the above and a person who is skilled in the art could easily carry out the operation based on a well-known technique shown in references such as Molecular Cloning, 3rd edition (Sambrook and Russell, CSHL PRESS).

The chemical synthesis is not particularly limited, and for example, a commercial peptide synthesis resin can be used to condense α-amino group and an amino acid having side-chain functional group protected as appropriate on the resin according to well-known various condensation methods. Further, when a novel functional group which natural amino acids do not have is introduced, the functional group can be introduced by peptide synthesis using as a material an amino acid derivative in which the functional group is inserted in advance, or by reaction of a predetermined compound with a peptide after peptide synthesis.

Labeling Reagent

In the embodiment, the labeling reagent is not particularly limited, and for example, dye, a particle, polyethylene glycol (PEG), phospholipid, PEG-phospholipid complex can be used.

Particularly preferable examples of the dye include fluorescent dye, in particular, near-infrared fluorescent dye such as indocyanine green (ICG), Alexa Fluor (registered trademark, distributed by Invitrogen Life Technologies) 750, Alexa Fluor 790, Vivotag 680 (trademark, distributed by Invitrogen Life Technologies), Vivotag-S (trademark, distributed by VisEn Medical Inc.) 680, Vivotag-5750, Amino-SPARK (trademark, distributed by VisEn Medical) 680, AminoSPARK750 (distributed by VisEn Medical, Inc.), DyLight (distributed by Thermo Fisher Scientific Inc.) 680, DyLight750, Dylight800 (distributed by Thermo Fisher Scientific, Inc.), IRDye (registered trademark, distributed by LI-COR Biosciences) 700DX, IRDye800CW, IRDye800RS (distributed by LI-COR Biosciences, Inc.), Cy (trademark, distributed by GE Healthcare UK Ltd.) 5.5 (distributed by GE Healthcare UK Ltd.).

Cyanine dye having absorption wavelength and fluorescence wavelength in the near-infrared is particularly preferable, and indocyanine green or its derivative, Alexa Fluor (registered trademark, distributed by Invitrogen Life Technologies) 750 is particularly preferable.

Preferable examples of the particle include a metal particle such as iron oxide and gold, a high molecular particle, a protein particle. In particular, iron oxide particle can be used for diagnosis application. Iron oxide particle for internal diagnosis has been already used clinically as a contrast agent of iron oxide magnetic resonance imaging and its average diameter is approximately 50 to 100 nm. Since capillary diameter is approximately 2 μm, the particle size is up to 1 μm or less. If tissue permeability is considered, its preferable size is 5 to 500 nm.

Furthermore, PEG and phospholipid are also effective as a labeling reagent for protein function control. It is known that PEG has low toxicity to a living organism and that PEG-labeling of a substance which is administered to a living organism prolongs its half-life in blood. PEG is a nonionic polymer having high water solubility and has a large excluded volume effect. In order to exert sufficient excluded volume effect of PEG, it is desirable that the average molecular weight of PEG should be 2 k or more. To suppress functional inhabitation of the protein to be labeled, it is desirable that the average molecular weight of PEG should be 40 k or less. Therefore, particularly preferably, the average molecular weight of PEG should be 2 k to 40 k. In addition, in the specification, polyethylene glycol (PEG) includes derivatives of PEG.

Compared with fluorescent dye, the iron oxide particle and PEG have considerably large molecular size (several to several dozen nm) and therefore, they become large steric hindrances to the affinity interaction domain. As a result, the affinity between the labeled protein and the affinity support notably decrease as compared with the affinity between the protein to be labeled and the affinity support.

In the embodiment, the phospholipid may be any of natural phospholipids, synthetic phospholipids and derivatives thereof. For example, phosphatidylcholine, phosphatidylethanolamine, diacyl glycerophosphoethanolamine, distearoylglycerophosphoethanolamine (DSPE), dimyristoylglycerophosphoethanolamine (DMPE), dipalmitoylglycerophosphoethanolamine (DPPE), dioleoylglycerophosphoethanolamine (DOPE), phosphatidylserine, phosphatidylinositol, phosphatidylglycerol, polyethylene glycol-phospholipid complex, and egg phospholipid can be included. Further, the above-mentioned phospholipid can contain a functional group forming a covalent bind with a ligand, such as an amino group, a hydroxyl group, a thiol group, a maleimide group, a carboxyl group, and a biotin group. In order to ensure stable introduction of hydrophobicity to a protein, in particular, polyethylene glycol-phospholipid complex (it may be referred to as pegylated phospholipid in the specification) can be utilized.

In the purification method according to the present embodiment, the labeled protein can be more effectively concentrated and purified with the above-mentioned labeling reagent.

Moreover, regarding the labeling reagent, a functional group for further connection with the labeling site may be attached to the above-mentioned labeling reagent. As such a functional group, for example, NHS ester, isocyanato, maleimide, hydrazide (aldehyde reactivity), an amino group, a carboxyl group, a thiol group, a hydroxyl group can be utilized.

Though the binding between the labeling site and the labeling reagent includes a covalent bind, an ionic bind and a coordinate bind and is not particularly limited, particularly preferably, a covalent bind is used. The labeling reagent may bind to the labeling site via a bifunctional crosslinking reagent such as 4-(maleimidomethyl)cyclohexane-1-carboxylic acid succinimide ester. For example, 4-(maleimidomethyl)cyclohexane-1-carboxylic acid succinimide ester modifies a thiol group of a cysteine side chain of the labeling site, and thereby can bind to an amino group of the labeling reagent via a hydroxysuccinimide group.

The labeled protein according to the present embodiment, as its feature, considerably differs from the protein to be labeled in a state without a label in the affinity for the affinity support. Though the affinity of the affinity interaction domain itself for the affinity support does not vary before and after labeling, the affinity for the affinity support varies before and after labeling from the viewpoint of the whole of the labeled protein. The affinity is generally evaluated by its dissociation constant $K_D$. However, in the light of the object of the present invention, which is separation of the labeled protein from the protein to be labeled, it is important that the protein to be labeled before labeling strongly binds to the affinity support; therefore, the association rate constant $K_{on}$, is more important than the dissociation constant $K_D$.

Preferably, the difference between the affinities is 10-folds. Namely, preferably, the difference of the association rate constant $K_{on}$ between the labeled protein and the affinity support from the association rate constant $K_{on}$ between the protein to be labeled and the affinity support is 10-fold. In particular, preferably, the affinity decreases after labeling, and preferably, the association rate constant $K_{on}$ between the labeled protein and the affinity support is 1/10 or less as compared with the association rate constant between the protein to be labeled and the affinity support. For example, the system in which $K_{on}$ between the protein to be labeled and the affinity support is $10^4$ $M^{-1}$ $s^{-1}$ ($K_{off}=10^{-4}$ $s^{-1}$, KD=$10^{-8}$ M) and $K_{on}$ between the labeled protein and the affinity support is $10^3$ $M^{-1}$ $s^{-1}$ ($K_{off}=10^{-4}$ s, KD=$10^{-7}$ M) is assumed. In the system, the total concentration of the affinity interaction domain of the labeled protein or the protein to be labeled is set to 1 μM, and the total concentration of the affinity support interacting the domain is set to 1 μM. For the sake of simplicity, assume that the affinity interaction domain and the affinity support interact by the ratio of 1:1. Under these conditions, when time-dependent change of binding of each affinity interaction domain and its affinity support is simulated, 83% of the protein to be labeled ($K_{on}=10^4$ $M^{-1}$ $s^{-1}$) binds to its affinity support after a 10-minute incubation. On the other hand, 36% of the labeled protein ($K_{on}=10^3$ $M^{-1}$ $s^{-1}$) binds to its affinity support. Accordingly, 10-fold difference of $K_{on}$ between the labeled protein and the affinity support from $K_{on}$ between the protein to be labeled and the affinity support is sufficient affinity difference to separate and purify the labeled protein and the protein to be labeled by affinity purification. As described below in the examples, labeling of the protein to be labeled according to the present embodiment causes a spatial inhibitory effect of the labeling reagent. As a result, its affinity for the affinity support considerably decreases. A labeled and an unlabeled matters can be easily separated by using this fact.

The affinity of the labeled protein depends on molecular sizes, spatial locations, numbers, charge states of the affinity interaction domain and the labeling reagent. It will be described below using an example in which the affinity interaction domain is hexa-histidine. The average distance of a peptide bind unit is approximately 0.38 nm, and the molecular length of hexa-histidine is approximately 2.3 nm. When the labeling reagent binds to a labeling site located within the distance of 0 to 5 residues from the hexa-histidine sequence, for example, cysteine, the labeling reagent having the molecular size of approximately 2 to 6 nm or more can exert steric inhibitory effect; this labeling reagent can be suitably used. The size of cyanine fluorescent dye is generally about 2 nm. When the cyanine fluorescent dye serves as a label in the vicinity to the hexa-histidine, it is preferable that the labeling should be carried out at the closest position possible, specifically, at the position within at least 5 amino acid residues therebetween. Not only the size and distance of a molecule, but the charge state of a molecule have an effect on the affinity. For example, when the affinity interaction domain has cationic charge and the labeling reagent has minus charge within the proper distance, the electrostatic interaction between the two occurs. Thus, the affinity of the labeled protein for the affinity support can be lowered effectively.

Figure 5:
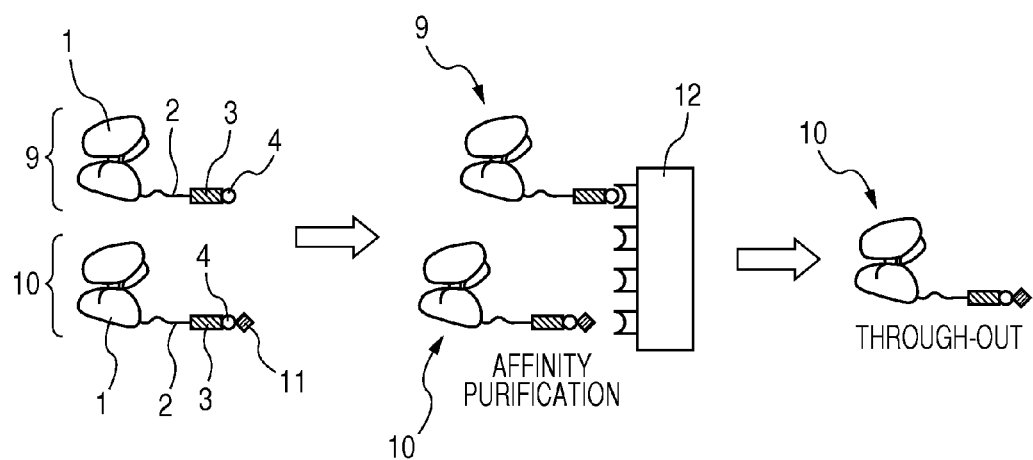
FIG. 5 is a diagram showing methods for obtaining a labeled protein according to the embodiment of the present invention.

The method for obtaining the labeled protein according to the present embodiment will be described below in detail with reference to FIG. 5. In the figure, 9, 10, and 12 represent a protein to be labeled, a labeled protein, a labeling reagent and an affinity support, respectively.

i) A step for obtaining a protein to be labeled 9 having a target protein 1, an affinity interaction domain 3 and a labeling site 4

Protein to be labeled 9 having target protein 1, affinity interaction domain 3 and labeling site 4 can be obtained according to the above-mentioned section of Protein to be labeled.

ii) A step for obtaining a labeled protein 10 connected to a labeling reagent 11 by connecting labeling reagent 11 to labeling site 4 of the protein to be labeled 9.

Labeled protein 10 can be obtained by connecting labeling reagent 11 to labeling site 4 of protein to be labeled 9 according to the section of Labeling reagent.

iii) A step for bringing the mixture of labeled protein 10 and protein to be labeled 9 without a labeling reagent into contact with an affinity support which can bind specifically to the affinity interaction domain.

As described above, compared with protein to be labeled 9, labeled protein 10 according to the present embodiment varies in its affinity for an affinity support 12 by labeling with labeling reagent 11. These steps are steps for separating labeled protein 10 using the affinity difference. The step iii) is, specifically, to bring the mixture of labeled protein 10 and protein to be labeled 9 into contact with affinity support 12 which will bind specifically to their affinity interaction domains. It is carried out, for example, by pouring the mixture into a column filled with the affinity support 12.

iv) A step for selecting labeled protein 10 by the difference between the affinities for affinity support 12.

When the difference between the affinities for affinity support is sufficiently large, and only protein to be labeled 9 binds to affinity support 12 while labeled protein 10 does not bind to affinity support 12, labeled protein 10 can be selected by collecting a fraction passing through the column. FIG. 5 illustrates this example. Furthermore, if necessary, the repetition of this operation enables labeled protein 10 with higher purity to be obtained.

On the other hand, when the difference between the affinities for the affinity support is not as large as the above, and labeled protein 10 weakly binds to the affinity support 12, labeled protein 10 can be selected by the following method. Namely, only the labeled protein can be selectively eluted by selecting each condition such as an eluent or elution time which elutes only labeled protein 10 but not protein to be labeled 9. As the eluent, for example, what contains a substance having affinity specific to the affinity support 12 can be used and it can be selected as appropriate based on affinity support 12 in use. For example, the affinity interaction domain is oligo-histidine, a solution containing imidazole or a derivative thereof can be used as the eluent. The step can be carried out according to other well-known methods for affinity purification.

EXAMPLES

Though the examples described below will show specific reagents and reactive conditions, these reagents and conditions can be variously modified. All of the modifications are also included in the scope of the present invention. The examples which follow are presented only to assist in understanding the invention, and are not to limit the scope of the invention.

Example 1

Preparation of Antibody hu4D5-8 scFv Containing an Affinity Interaction Domain and a Labeling Site A gene hu4D5-8 scFv encoding a single-chain antibody (scFv) was prepared based on the gene sequence (hu4D5-8) of the variable region of IgG where HER2 was supposed to bind. First, a cDNA in which VL and VH genes of hu4D5-8 were connected by a cDNA encoding peptide (GGGGS)$_3$ was prepared. The restriction enzyme NcoI recognition site and the restriction enzyme NotI recognition site were introduced at the 5' terminus and 3' terminus, respectively. The nucleotide sequence will be shown as follows (the part of the restriction enzyme recognition site is underlined):

(SEQ ID NO: 18)

```
5'-
CCATGGATATCCAGATGACCCAGTCCCCGAGCTCCCTGTCCGCCTCTGTGGGCGATAGG

GTCACCATCACCTGCCGTGCCAGTCAGGATGTGAATACTGCTGTAGCCTGGTATCAACA

GAAACCAGGAAAAGCTCCGAAACTACTGATTTACTCGGCATCCTTCCTCTACTCTGGAG

TCCCTTCTCGCTTCTCTGGATCCAGATCTGGGACGGATTTCACTCTGACCATCAGCAGT
```

-continued
```
CTGCAGCCGGAAGACTTCGCAACTTATTACTGTCAGCAACATTATACTACTCCTCCCAC

GTTCGGACAGGGTACCAAGGTGGAGATCAAAGGCGGTGGTGGCAGCGGTGGCGGTGGCA

GCGGCGGTGGCGGTAGCGAGGTTCAGCTGGTGGAGTCTGGCGGTGGCCTGGTGCAGCCA

GGGGGCTCACTCCGTTTGTCCTGTGCAGCTTCTGGCTTCAACATTAAAGACACCTATAT

ACACTGGGTGCGTCAGGCCCCGGGTAAGGGCCTGGAATGGGTTGCAAGGATTTATCCTA

CGAATGGTTATACTAGATATGCCGATAGCGTCAAGGGCCGTTTCACTATAAGCGCAGAC

ACATCCAAAAACACAGCCTACCTGCAGATGAACAGCCTGCGTGCTGAGGACACTGCCGT

CTATTATTGTTCTAGATGGGGAGGGGACGGCTTCTATGCTATGGACTACTGGGGTCAAG

GAACCCTGGTCACCGTCTCCTCGGCGGCCGC-3'.
```

The above-mentioned gene fragment hu4D5-8 scFv was inserted downstream of T7/lac promoter of plasmid pET-22b (+) (distributed by Novagen Inc.). More specifically, ligation of the above-mentioned cDNA into plasmid pET-22b (+) (distributed by Novagen Inc.) digested with the restriction enzymes NcoI and NotI was carried out.

Then, a sequence containing those of the affinity interaction domain and the labeling site was inserted. As a specific example, the tag sequence (Ala-Ala-Ala-Leu-Glu-His-His-His-His-His-His-Gly-Gly-Cys (SEQ ID NO: 6)) having a cysteine residue as a labeling site and 6×His tag, which is six continuous histidine residues for affinity purification, at the carboxy terminus of the above-mentioned gene product will be described. First, the above plasmid was digested with the restriction enzymes NotI and XhoI. A double-stranded DNA was obtained by annealing of the synthetic DNAs (SEQ ID NO: 19 and SEQ ID NO: 20) having the nucleotide sequences shown below. After the DNA thus obtained was digested with the restriction enzymes NotI and XhoI, the ligation of the DNA into the above plasmid was carried out. As a result, a plasmid for expression of a protein having a sequence containing the affinity interaction domain and the labeling site according to the present example fused at the carboxy terminus of the single-chain antibody (scFv) which would bind to HER2, was prepared.

(SEQ ID NO: 19)
5'-GGCCGCACTGGAACACCATCACCATCACCATGGTGGTTGTTGAT
GAC-3'

(SEQ ID NO: 20)
5'-TCGAGTCATCAACAACCACCATGGTGATGGTGATGGTGTTCCAGT
GC-3'

Figure 2:
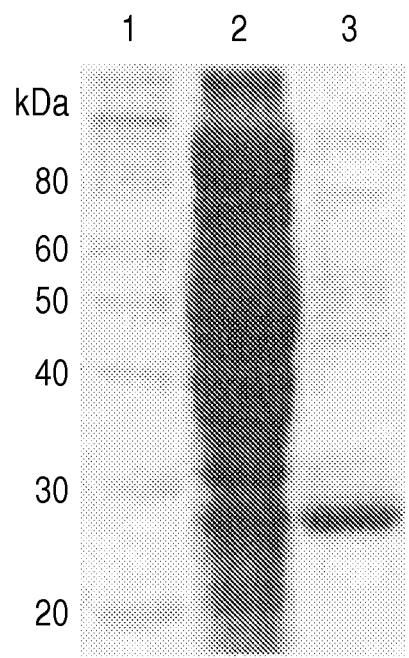
FIG. 2 is the result of gel electrophoresis of hu4D5-8 scF proteins before and after purification under reduction with metal chelate affinity chromatography.
Figure 3:
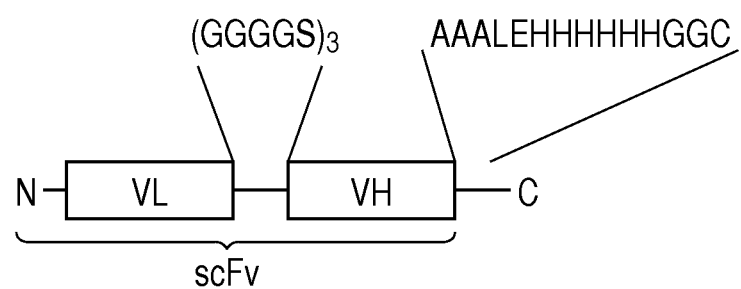
FIG. 3 is a schematic diagram of a labeled protein including a single-chain antibody and a sequence having an affinity interaction domain and a labeling site.

The plasmid was transformed into E. coli (Escherichia coli BL21(DE3)) to obtain strains for expression. The strains thus obtained were precultured in a 4 ml LB-Amp culture overnight. Then, the total amount was added to a 250 ml 2×YT culture and shaking-cultured at 28° C. and 120 rpm for 8 hours. Thereafter, IPTG was added at a final concentration of 1 mM and the strains were cultured overnight at 28° C. The cultured E. coli was centrifuged at 8000×g and 4° C. for 30 min and the supernate medium was collected. Thereto added 60% by weight of ammonium sulfate based on the medium thus obtained and a protein was precipitated by salt precipitation. After the solution obtained by the salt precipitation was left to stand overnight at 4° C., the precipitate was collected by centrifuging at 8000×g and 4° C. for 30 min. The resultant precipitate was dissolved in a buffer (20 mM Tris-HCl, 500 mM NaCl) and dialyzed against 1 L of the same buffer. The protein solution obtained by the dialysis was added to a column filled with His-Bind (registered trademark) Resin (distributed by Novagen Inc.) and purified by metal chelate affinity chromatography with Ni ion. It was confirmed that the purified hu4D5-8 scFv gave a single band on reducing SDS-PAGE and its molecular weight was approximately 28 kDa. FIG. 2 illustrates the result. In FIG. 2, lane 1 illustrates the result of loading a molecular-weight marker (Bench-Mark™ His-Tag standard (distributed by Invitrogen Life Technologies)); lane 2 illustrates the result of loading the protein solution before purification; and lane 3 illustrates the result of the protein solution after purification (28 kDa). FIG. 3 illustrates a schematic diagram of a expressed protein (a single-chain antibody) having a sequence containing an affinity interaction domain and a labeling site. In FIG. 3, VL and VH domains of the antibody, a peptide linker connecting these domains, and further, the sequence containing the affinity interaction domain and the labeling site are connected to the carboxy terminus. The example of the amino acid sequence of the prepared antibody will be shown as follows (the sequence containing the affinity interaction domain and the labeling site is underlined):

(SEQ ID NO: 21)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASGFN

IKDTYIHWVRQAPGKGLEWVARIYPTNGYTRYADSVKGRFTISADTSKNT

AYLQMNSLRAEDTAVYYCSRWGGDGFYAMDYWGQGTLVTVSS

AAALEHHHHHHGGC.

Hereinafter, the resultant protein is referred to as an antibody.

Example 2

Labeling with Antibody Dye

The antibody prepared above was reduced and treated with 20 fold molar amount of tris(2-carboxyethyl)phosphine hydrochloride (TCEP) at 25° C. for 2 hours after buffer replacement with a phosphate buffer containing 5 mM EDTA (2.68 mM KCl/137 mM NaCl/1.47 mM KH$_2$PO$_4$/1 mM Na$_2$HPO$_4$/5 mM EDTA, pH 7.4). The resultant antibody was reacted with 10 fold molar amount of fluorescent dye, Alexa Fluor (registered trademark, distributed by Invitrogen Life Technologies) 750-maleimide at 25° C. for 2 to 4 hours. After 1 hour reaction, unreacted Alexa Fluor (registered trademark, distributed by Invitrogen Life Technologies) 750-maleimide was removed by gel filtration chromatography with Superdex 200 GL 10/300 column (manufactured by GE Healthcare UK Ltd.) to obtain a labeled antibody (hereinafter, referred to as a dye-labeled antibody). The labeling index (molar ratio) of the dye to the antibody was 0.4 to 0.6 according to absorbance determination.

Example 3

Labeling of an Antibody with PEG

Figure 4:
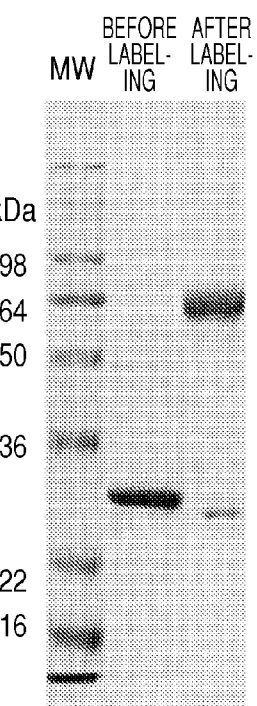
FIG. 4 shows the reduced SDS-PAGE results of a pegylated antibody and an antibody before pegylation prepared in the example.

The antibody prepared above was reduced and treated with 20 fold molar amount of tris(2-carboxyethyl)phosphine hydrochloride (TCEP) at 25° C. for 2 to 4 hours after buffer replacement with a phosphate buffer containing 5 mM EDTA (2.68 mM KCl/137 mM NaCl/1.47 mM $KH_2PO_4$/1 mM $Na_2HPO_4$/5 mM EDTA, pH 7.4). The resultant antibody was reacted with 10 fold molar amount of 20 kDa PEG-maleimide (distributed by NOF CORPORATION) at 25° C. for 2 to 4 hours. After the reaction, unreacted 20 kDa PEG-maleimide was removed by gel filtration chromatography with Superdex 200 GL 10/300 column (manufactured by GE Healthcare UK Ltd.) to obtain a pegylated antibody. Preparation of the Pegylated Antibody can be Confirmed by comparison with the molecular weight of the antibody before pegylation by SDS-PAGE. FIG. 4 illustrates the reducing SDS-PAGE results of the pegylated antibody prepared in the present example and the antibody before pegylation.

Example 4

Labeling of an Antibody with a Particle

The antibody prepared above was reduced and treated with 20 fold molar amount of tris(2-carboxyethyl)phosphine hydrochloride (TCEP) at 25° C. for 2 to 4 hours after buffer replacement with a phosphate buffer containing 5 mM EDTA (2.68 mM KCl/137 mM NaCl/1.47 mM $KH_2PO_4$/1 mM $Na_2HPO_4$/5 mM EDTA, pH 7.4). The resultant antibody was reacted with a commercial iron oxide particle, nanomag-D-SPIO (a maleimide-PEG particle, average diameter of 20 nm, distributed by Corefront Corporation) at 25° C. for 2 to 4 hours. After the reaction, the immobilization of the antibody on the particle can be confirmed by determining the amount of the antibody immobilized on the particle by BCA assay or the like.

Example 5

Evaluation of the Affinities Between an Affinity Support and an Antibodies Before and after Labeling The interaction between the labeled antibody prepared above and an affinity support, Ni-NTA was measured by Biacore X system (distributed by GE Healthcare UK Ltd.). A carboxymethyl dextran chip (distributed by GE Healthcare UK Ltd.) having nitrilotriacetic acid (NTA) immobilized thereon beforehand was used as a sensor chip and an Ni salt solution was added thereto to form a nitrilotriacetic acid (NTA)-nickel complex on the surface. The result was approximately 80 RU. PBS-T (2.68 mM KCl/137 mM NaCl/1.47 mM $KH_2PO_4$/1 mM $Na_2HPO_4$/0.005% Tween 20, pH 7.4) was used as a running buffer and 100 nM of the labeled antibody or unlabeled antibody (a control) was injected at a flow rate of 30 ul/min to evaluate the binding capacity.

Regarding measuring time, the injection time (binding) was 120 seconds and the elapsed time after stopping the injection (unbinding) was 120 seconds. The flow cell surface was washed every time 1 sample was measured by injecting proper amount of an EDTA solution until the sensorgram returned to baseline. In the binding kinetic analysis experiment, the sensorgram was analyzed with a 1:1 Langmuir fitting model of BIAevaluation 3.0.2 software (distributed by GE Healthcare UK Ltd.). The amount of adsorption (resonance unit: RU) of the labeled antibody into the sensor surface decreased approximately 10 fold compared to the control. This result shows that dye labeling decreases the affinity between an oligohistidine and an NTA-nickel complex.

Example 6

Concentration and Purification of a Labeled Protein by Affinity Purification

As a affinity support, a metal chelate column carrier, His-Bind (manufactured by Novagen Inc.) is used. Steps for preparing a column, loading a sample, and washing are performed at room temperature (20° C.) in accordance with the method recommended by the manufacturer. However, the condition can be optimized as necessary.

First, the labeled proteins prepared in the Examples 2 to 4 are added to an Ni-charged His-Bind column. Tris buffer solution is used as a developing solvent. All of the solution passing through the column is collected. The labeled protein which is the target is contained in the solution. An unlabeled protein is strongly held in the column. When the labeled protein which is the target is not released, the addition of a low concentration of imidazole solution, for example, the concentration of 5 mM-50 mM, enables the collection of the labeled protein which is the target. On the other hand, the unlabeled protein held in the column can be collected by eluting it in a 100 mM-1 M concentration imidazole solution. The purification of the labeled protein can be confirmed by ultraviolet-visible absorption spectrum of the collected solution or SDS-PAGE. If necessary, the repetition of the above purifying operation can improve the purification degree.

Example 7

Oligo DNA for Preparing a Sequence Containing a Affinity Interaction Domain and a Labeling Site as a Fusion Protein Oligo DNAs according to the example, for preparing a sequence containing the affinity interaction domain and the labeling site as a fusion protein, will be shown below. According to Example 1, ligation reaction connects the oligo DNAs with antibody genes.

Regarding the sequence, Ala-Ala-Ala-Leu-Glu-His-His-His-His-His-His-Cys (SEQ ID NO: 7), its expression construct can be prepared by cassette ligation with restriction enzymes NotI and XhoI after obtaining a double-stranded DNA by annealing the following sequences:

```
                                            (SEQ ID NO: 22)
5'-GGCCGCACTGGAACACCATCACCATCACCATTGTTGATGAC-3';
and
                                            (SEQ ID NO: 23)
5'-TCGAGTCATCAACAATGGTGATGGTGATGGTGTTCCAGTGC-3'.
```

Regarding the sequence, Ala-Ala-Ala-Leu-Glu-Cys-His-His-His-His-His-His (SEQ ID NO: 8), its expression construct can be prepared by cassette ligation with restriction enzymes NotI and XhoI after obtaining a double-stranded DNA by annealing the following sequences:

(SEQ ID NO: 24)
5'-GGCCGCACTGGAATGTCACCATCACCATCACCATTGATGAC-3';
and (SEQ ID NO: 25)
5'-TCGAGTCATCAATGGTGATGGTGATGGTGACATTCCAGTGC-3'.

Regarding the sequence, Ala-Ala-Ala-Leu-Glu-Cys-His-His-His-His-His-His-Cys (SEQ ID NO: 9), its expression construct can be prepared by cassette ligation with restriction enzymes NotI and XhoI after obtaining a double-stranded DNA by annealing the following sequences:

(SEQ ID NO: 26)
5'-GGCCGCACTGGAATGTCACCATCACCATCACCATTGTTGATGAC-3';
and (SEQ ID NO: 27)
5'-TCGAGTCATCAACAATGGTGATGGTGATGGTGACATTCCAGTGC-3'.

Regarding the sequence, Ala-Ala-Ala-Leu-Glu-Cys-His-His-His-His-His-His-Gly-Gly-Cys (SEQ ID NO: 10), its expression construct can be prepared by cassette ligation with restriction enzymes NotI and XhoI after obtaining a double-stranded DNA by annealing the following sequences:

(SEQ ID NO: 28)
5'-GGCCGCACTGGAATGTCACCATCACCATCACCATGGTGGTTGTTGATGAC-3';
and (SEQ ID NO: 29)
5'-TCGAGTCATCAACAACCACCATGGTGATGGTGATGGTGACATTCCAGTGCGGC-3'.

Regarding the sequence, Ala-Ala-Ala-Cys-His-His-His-His-His-His (SEQ ID NO: 11), its expression construct can be prepared by cassette ligation with restriction enzymes NotI and XhoI after obtaining a double-stranded DNA by annealing the following sequences:

(SEQ ID NO: 30)
5'-GGCCGCATGTCACCATCACCATCACCATTGATGAC-3';
and (SEQ ID NO: 31)
5'-TCGAGTCATCAATGGTGATGGTGATGGTGACATGC-3'.

Regarding the sequence, Ala-Ala-Ala-Gly-Cys-Gly-Gly-Leu-Glu-His-His-His-His-His-His (SEQ ID NO: 12), its expression construct can be prepared by cassette ligation with restriction enzymes NotI and XhoI after obtaining a double-stranded DNA by annealing the following sequences:

(SEQ ID NO: 32)
5'-GGCCGCAGGTTGTGGTGGTC-3';
and (SEQ ID NO: 33)
5'-TCGAGACCACCACAACCTGC-3'.

Regarding the sequence, Ala-Ala-Ala-Cys-Leu-Glu-His-His-His-His-His-His (SEQ ID NO: 13), its expression construct can be prepared by cassette ligation with restriction enzymes NotI and XhoI after obtaining a double-stranded DNA by annealing the following sequences:

(SEQ ID NO: 34)
5'-GGCCGCATGTC-3';
and (SEQ ID NO: 35)
5'-TCGAGACATGC-3'.

Regarding the sequence, Ala-Ala-Ala-Leu-Cys-His-His-His-His-His-His (SEQ ID NO: 14), its expression construct can be prepared by cassette ligation with restriction enzymes NotI and XhoI after obtaining a double-stranded DNA by annealing the following sequences:

(SEQ ID NO: 36)
5'-GGCCGCACTGTGTCACCATCACCATCACCATTGATGAC-3';
and (SEQ ID NO: 37)
5'-TCGAGTCATCAATGGTGATGGTGATGGTGACACAGTGC-3'.

Example 8

Labeling of an Antibody with a Polyethyleneglycol-Phospholipid Complex

The antibody prepared above was reduced and treated with 20 fold molar amount of tris(2-carboxyethyl)phosphine hydrochloride (TCEP) at 25° C. for 2 hours after buffer replacement with a phosphate buffer containing 5 mM EDTA (2.68 mM KCl/137 mM NaCl/1.47 mM $KH_2PO_4$/1 mM $Na_2HPO_4$/5 mM EDTA, pH 7.4). The resultant antibody was reacted with 4 fold molar amount of [N-[(3-Maleimide-1-oxopropyl)aminopropyl polyethyleneglycol-carbamyl]distearoylphosphatidyl-ethanolamine (DSPE-PEG-MAL)] (product name, SUNBRIGHT® DSPE-020MA, distributed by NOF CORPORATION) at 25° C. for 4 hours. After the reaction, a partially purified antibody labeled with a polyethyleneglycol-phospholipid complex was obtained by gel filtration chromatography with Superdex 200 GL 10/300 column (manufactured by GE Healthcare UK Ltd.).

Example 9

Concentration/Purification of a Dye-Labeled Antibody by Affinity Purification

As a sample, a dye-labeled antibody having a 0.43 labeling index (molar ratio) of dye to an antibody was used. To an His-Bind column (produced by Novagen Inc.) which was charged with Ni beforehand was added 1 mL of a solution of the dye-labeled antibody (carrier bed volume: 1 mL). Next, mL of Tris buffer solution (pH 8.0) as a developing solvent was added thereto and all of the solution passing through the column (referred to as a passing solution) was collected. The dye-labeled antibody which was the target was contained in the solution. An unlabeled antibody without dye-labeling was strongly held in the column. The labeling index of the labeled antibody calculated by ultraviolet-visible absorption spectrum of the passing solution was 0.58. On the other hand, the unlabeled antibody held in the column was collected by eluting it in a 300 mM imidazole solution. It was confirmed that the antibody in the collected solution was not dye-labeled by the ultraviolet-visible absorption spectrum of the collected solution. These results show that the purification method of the present example can easily remove an unlabeled antibody from a labeled antibody.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-159859, filed Jul. 6, 2009, which is hereby incorporated by reference herein in its entirety.

What is claimed is:

1. A labeled protein comprising:

a protein to be labeled having a target protein, at least one or more affinity interaction domains for binding to an affinity support, and at least one or more labeling sites; and a labeling reagent binding to at least one of the labeling sites;

wherein the affinity of the labeled protein for the affinity support differs from that of the protein to be labeled for the affinity support, wherein the protein to be labeled comprises, as a sequence comprising the at least one or more affinity interaction domains and the at least one or more labeling sites, an amino acid sequence which isselected from the group consisting of SEQ ID NOs: 1 and 4 to 5:

```
                                              (SEQ ID NO: 1)
His-His-His-His-His-His-Gly-Gly-Cys;

(SEQ ID NO: 4)
Cys-His-His-His-His-His-His-Cys;
and (SEQ ID NO: 5)
Cys-His-His-His-His-His-His-Gly-Gly-Cys.
``` wherein the labeling reagent comprises at least one selected from the group consisting of dye, particle, phospholipid and polyethylene glycol-phospholipid complex.

2. A labeled protein comprising:

a protein to be labeled having a target protein, at least one or more affinity interaction domains for binding to an affinity support, and at least one or more labeling sites; and a labeling reagent binding to at least one of the labeling sites;

wherein the affinity of the labeled protein for the affinity support differs from that of the protein to be labeled for the affinity support, wherein the protein to be labeled comprises, as a sequence comprising the at least one or more affinity interaction domains and the at least one or more labeling sites, an amino acid sequence which is selected from the group consisting of SEQ ID NOs: 6 to 14:

```
                                              (SEQ ID NO: 6)
Ala-Ala-Ala-Leu-Glu-His-His-His-His-His-His-Gly-
Gly-Cys;

(SEQ ID NO: 7)
Ala-Ala-Ala-Leu-Glu-His-His-His-His-His-Cys;

(SEQ ID NO: 8)
Ala-Ala-Ala-Leu-Glu-Cys-His-His-His-His-His-His;

(SEQ ID NO: 9)
Ala-Ala-Ala-Leu-Glu-Cys-His-His-His-His-His-
Cys;

(SEQ ID NO: 10)
Ala-Ala-Ala-Leu-Glu-Cys-His-His-His-His-His-
Gly-Gly-Cys;

(SEQ ID NO: 11)
Ala-Ala-Ala-Cys-His-His-His-His-His-His;

(SEQ ID NO: 12)
Ala-Ala-Ala-Gly-Cys-Gly-Gly-Leu-Glu-His-His-His-
His-His-His;

(SEQ ID NO: 13)
Ala-Ala-Ala-Cys-Leu-Glu-His-His-His-His-His-His;
and (SEQ ID NO: 14)
Ala-Ala-Ala-Leu-Cys-His-His-His-His-His-His.
``` wherein the labeling reagent comprises at least one selected from the group consisting of dye, particle, phospholipid and polyethylene glycol-phospholipid complex.

3. The labeled protein according to claim 1, wherein association rate constant $K_{on}$ between the labeled protein and the affinity support is $1/10$ or less as compared with association rate constant between the protein to be labeled and the affinity support.

4. The labeled protein according to claim 1, wherein the target protein is a single-chain antibody.

5. A labeled protein comprising a protein to be labeled having a target protein, at least one or more affinity interaction domains for binding to an affinity support, and at least one or more labeling sites; and a labeling reagent binding to at least one of the labeling sites;

wherein the affinity of the labeled protein for the affinity support differs from that of the protein to be labeled for the affinity support, wherein the target protein is a polypeptide comprising an amino acid sequence of SEQ ID NO: 38:

```
                                              (SEQ ID NO: 38)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKGGGGSGGGGSGGGGSEVQLVESGGGLVQPGGSLRLSCAASGFN

IKDTYIHWVRQAPGKGLEWVARIYPTNGYTRYADSVKGRFTISADTSKNT

AYLQMNSLRAEDTAVYYCSRWGGDGFYAMDYWGQGTLVTVSS.
```

\* \* \* \* \*

SEQUENCE LISTING

```
<160> NUMBER OF SEQ ID NOS: 38

<210> SEQ ID NO 1
<211> LENGTH: 9
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 1

His His His His His His Gly Gly Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 2

His His His His His His Cys
1               5

<210> SEQ ID NO 3
<211> LENGTH: 7
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 3

Cys His His His His His His
1               5

<210> SEQ ID NO 4
<211> LENGTH: 8
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 4

Cys His His His His His His Cys
1               5

<210> SEQ ID NO 5
<211> LENGTH: 10
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 5
```

Cys His His His His His Gly Gly Cys
1               5                  10

<210> SEQ ID NO 6
<211> LENGTH: 14
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 6

Ala Ala Ala Leu Glu His His His His His His Gly Gly Cys
1               5                  10

<210> SEQ ID NO 7
<211> LENGTH: 12
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 7

Ala Ala Ala Leu Glu His His His His His His Cys
1               5                  10

<210> SEQ ID NO 8
<211> LENGTH: 12
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 8

Ala Ala Ala Leu Glu Cys His His His His His
1               5                  10

<210> SEQ ID NO 9
<211> LENGTH: 13
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 9

Ala Ala Ala Leu Glu Cys His His His His His Cys
1               5                  10

<210> SEQ ID NO 10
<211> LENGTH: 15
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 10

Ala Ala Ala Leu Glu Cys His His His His His Gly Gly Cys
1               5                  10                  15

<210> SEQ ID NO 11
<211> LENGTH: 10
<212> TYPE: PRT
<213> ORGANISM: Artificial Sequence
<220> FEATURE:

```
<223> OTHER INFORMATION: Sequence comprising affinity interaction domain
      and labeling site

<400> SEQUENCE: 11

Ala Ala Ala Cys His His His His His His
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 12

Ala Ala Ala Gly Cys Gly Gly Leu Glu His His His His His His
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 13

Ala Ala Ala Cys Leu Glu His His His His His His
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Sequence comprising affinity interaction domain
      and labeling site

<400> SEQUENCE: 14

Ala Ala Ala Leu Cys His His His His His His
1               5                   10

<210> SEQ ID NO 15
<211> LENGTH: 4
<212> TYPE: PRT
<213> ORGANISM: Artificial Sequence
<220> FEATURE:
<223> OTHER INFORMATION: Linker

<400> SEQUENCE: 15

Gly Gly Gly Gly
1

<210> SEQ ID NO 16
<211> LENGTH: 5
<212> TYPE: PRT
<213> ORGANISM: Artificial Sequence
<220> FEATURE:
<223> OTHER INFORMATION: Linker

<400> SEQUENCE: 16

Gly Gly Gly Gly Ser
1               5

<210> SEQ ID NO 17
<211> LENGTH: 5
```

```
<212> TYPE: PRT
<213> ORGANISM: Artificial Sequence
<220> FEATURE:
<223> OTHER INFORMATION: Linker

<400> SEQUENCE: 17

Ala Ala Ala Leu Glu
1               5

<210> SEQ ID NO 18
<211> LENGTH: 739
<212> TYPE: DNA
<213> ORGANISM: Artificial Sequence
<220> FEATURE:
<223> OTHER INFORMATION: recombinant scFv

<400> SEQUENCE: 18
ccatggatat ccagatgacc cagtccccga gctccctgtc cgcctctgtg ggcgataggg      60
tcaccatcac ctgccgtgcc agtcaggatg tgaatactgc tgtagcctgg tatcaacaga    120
aaccaggaaa agctccgaaa ctactgattt actcggcatc cttcctctac tctggagtcc    180
cttctcgctt ctctggatcc agatctggga cggatttcac tctgaccatc agcagtctgc    240
agccggaaga cttcgcaact tattactgtc agcaacatta tactactcct cccacgttcg    300
gacagggtac caaggtggag atcaaaggcg gtggtggcag cggtggcggt ggcagcggcg    360
gtggcggtag cgaggttcag ctggtggagt ctggcggtgg cctggtgcag ccagggggct    420
cactccgttt gtcctgtgca gcttctggct tcaacattaa agacacctat atacactggg    480
tgcgtcaggc cccgggtaag ggcctggaat gggttgcaag gatttatcct acgaatggtt    540
atactagata tgccgatagc gtcaagggcc gtttcactat aagcgcagac acatccaaaa    600
acacagccta cctgcagatg aacagcctgc gtgctgagga cactgccgtc tattattgtt    660
ctagatgggg aggggacggc ttctatgcta tggactactg gggtcaagga accctggtca    720
ccgtctcctc ggcggccgc                                                  739

<210> SEQ ID NO 19
<211> LENGTH: 47
<212> TYPE: DNA
<213> ORGANISM: Artificial Sequence
<220> FEATURE:
<223> OTHER INFORMATION: Synthesized DNA

<400> SEQUENCE: 19
ggccgcactg gaacaccatc accatcacca tggtggttgt tgatgac                    47

<210> SEQ ID NO 20
<211> LENGTH: 47
<212> TYPE: DNA
<213> ORGANISM: Artificial Sequence
<220> FEATURE:
<223> OTHER INFORMATION: Synthesized DNA

<400> SEQUENCE: 20
tcgagtcatc aacaaccacc atggtgatgg tgatggtgtt ccagtgc                    47

<210> SEQ ID NO 21
<211> LENGTH: 256
<212> TYPE: PRT
<213> ORGANISM: Artificial Sequence
<220> FEATURE:
<223> OTHER INFORMATION: Recombinant scFV comprising affinity
      interaction domain and labeling site
<220> FEATURE:
```

<220> FEATURE:
<221> NAME/KEY: MISC_FEATURE
<222> LOCATION: (243)..(256)
<220> FEATURE:
<221> NAME/KEY: MISC_FEATURE
<222> LOCATION: (243)..(256)
<223> OTHER INFORMATION: Affinity interaction domain and the labeling site

<400> SEQUENCE: 21

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Gly Gly Gly Gly Ser
            100                 105                 110
Gly Gly Gly Gly Ser Gly Gly Gly Ser Glu Val Gln Leu Val Glu
        115                 120                 125
Ser Gly Gly Gly Leu Val Gln Pro Gly Gly Ser Leu Arg Leu Ser Cys
130                 135                 140
Ala Ala Ser Gly Phe Asn Ile Lys Asp Thr Tyr Ile His Trp Val Arg
145                 150                 155                 160
Gln Ala Pro Gly Lys Gly Leu Glu Trp Val Ala Arg Ile Tyr Pro Thr
                165                 170                 175
Asn Gly Tyr Thr Arg Tyr Ala Asp Ser Val Lys Gly Arg Phe Thr Ile
            180                 185                 190
Ser Ala Asp Thr Ser Lys Asn Thr Ala Tyr Leu Gln Met Asn Ser Leu
        195                 200                 205
Arg Ala Glu Asp Thr Ala Val Tyr Tyr Cys Ser Arg Trp Gly Gly Asp
    210                 215                 220
Gly Phe Tyr Ala Met Asp Tyr Trp Gly Gln Gly Thr Leu Val Thr Val
225                 230                 235                 240
Ser Ser Ala Ala Ala Leu Glu His His His His His Gly Gly Cys
                245                 250                 255
```

<210> SEQ ID NO 22
<211> LENGTH: 41
<212> TYPE: DNA
<213> ORGANISM: Artificial Sequence
<220> FEATURE:
<223> OTHER INFORMATION: Synthesized DNA

<400> SEQUENCE: 22
ggccgcactg gaacaccatc accatcacca ttgttgatga c                41

<210> SEQ ID NO 23
<211> LENGTH: 41
<212> TYPE: DNA
<213> ORGANISM: Artificial Sequence
<220> FEATURE:
<223> OTHER INFORMATION: Synthesized DNA

<400> SEQUENCE: 23
tcgagtcatc aacaatggtg atggtgatgg tgttccagtg c                    41

<210> SEQ ID NO 24
<211> LENGTH: 41
<212> TYPE: DNA
<213> ORGANISM: Artificial Sequence
<220> FEATURE:
<223> OTHER INFORMATION: Synthesized DNA

<400> SEQUENCE: 24
ggccgcactg gaatgtcacc atcaccatca ccattgatga c                    41

<210> SEQ ID NO 25
<211> LENGTH: 41
<212> TYPE: DNA
<213> ORGANISM: Artificial Sequence
<220> FEATURE:
<223> OTHER INFORMATION: Synthesized DNA

<400> SEQUENCE: 25
tcgagtcatc aatggtgatg gtgatggtga cattccagtg c                    41

<210> SEQ ID NO 26
<211> LENGTH: 44
<212> TYPE: DNA
<213> ORGANISM: Artificial Sequence
<220> FEATURE:
<223> OTHER INFORMATION: Synthesized DNA

<400> SEQUENCE: 26
ggccgcactg gaatgtcacc atcaccatca ccattgttga tgac                 44

<210> SEQ ID NO 27
<211> LENGTH: 44
<212> TYPE: DNA
<213> ORGANISM: Artificial Sequence
<220> FEATURE:
<223> OTHER INFORMATION: Synthesized DNA

<400> SEQUENCE: 27
tcgagtcatc aacaatggtg atggtgatgg tgacattcca gtgc                 44

<210> SEQ ID NO 28
<211> LENGTH: 50
<212> TYPE: DNA
<213> ORGANISM: Artificial Sequence
<220> FEATURE:
<223> OTHER INFORMATION: Synthesized DNA

<400> SEQUENCE: 28
ggccgcactg gaatgtcacc atcaccatca ccatggtggt tgttgatgac           50

<210> SEQ ID NO 29
<211> LENGTH: 53
<212> TYPE: DNA
<213> ORGANISM: Artificial Sequence
<220> FEATURE:
<223> OTHER INFORMATION: Synthesized DNA

<400> SEQUENCE: 29
tcgagtcatc aacaaccacc atggtgatgg tgatggtgac attccagtgc ggc        53

<210> SEQ ID NO 30
<211> LENGTH: 35
<212> TYPE: DNA

<213> ORGANISM: Artificial Sequence
<220> FEATURE:
<223> OTHER INFORMATION: Synthesized DNA

<400> SEQUENCE: 30
ggccgcatgt caccatcacc atcaccattg atgac                35

<210> SEQ ID NO 31
<211> LENGTH: 35
<212> TYPE: DNA
<213> ORGANISM: Artificial Sequence
<220> FEATURE:
<223> OTHER INFORMATION: Synthesized DNA

<400> SEQUENCE: 31
tcgagtcatc aatggtgatg gtgatggtga catgc                35

<210> SEQ ID NO 32
<211> LENGTH: 20
<212> TYPE: DNA
<213> ORGANISM: Artificial Sequence
<220> FEATURE:
<223> OTHER INFORMATION: Synthesized DNA

<400> SEQUENCE: 32
ggccgcaggt tgtggtggtc                                 20

<210> SEQ ID NO 33
<211> LENGTH: 20
<212> TYPE: DNA
<213> ORGANISM: Artificial Sequence
<220> FEATURE:
<223> OTHER INFORMATION: Synthesized DNA

<400> SEQUENCE: 33
tcgagaccac cacaacctgc                                 20

<210> SEQ ID NO 34
<211> LENGTH: 11
<212> TYPE: DNA
<213> ORGANISM: Artificial Sequence
<220> FEATURE:
<223> OTHER INFORMATION: Synthesized DNA

<400> SEQUENCE: 34
ggccgcatgt c                                          11

<210> SEQ ID NO 35
<211> LENGTH: 11
<212> TYPE: DNA
<213> ORGANISM: Artificial Sequence
<220> FEATURE:
<223> OTHER INFORMATION: Synthesized DNA

<400> SEQUENCE: 35
tcgagacatg c                                          11

<210> SEQ ID NO 36
<211> LENGTH: 38
<212> TYPE: DNA
<213> ORGANISM: Artificial Sequence
<220> FEATURE:
<223> OTHER INFORMATION: Synthesized DNA

<400> SEQUENCE: 36
ggccgcactg tgtcaccatc accatcacca ttgatgac              38

```
<210> SEQ ID NO 37
<211> LENGTH: 38
<212> TYPE: DNA
<213> ORGANISM: Artificial Sequence
<220> FEATURE:
<223> OTHER INFORMATION: Synthesized DNA

<400> SEQUENCE: 37
tcgagtcatc aatggtgatg gtgatggtga cacagtgc                              38

<210> SEQ ID NO 38
<211> LENGTH: 242
<212> TYPE: PRT
<213> ORGANISM: Artificial Sequence
<220> FEATURE:
<223> OTHER INFORMATION: Target protein

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Val Glu
        115                 120                 125

Ser Gly Gly Gly Leu Val Gln Pro Gly Gly Ser Leu Arg Leu Ser Cys
    130                 135                 140

Ala Ala Ser Gly Phe Asn Ile Lys Asp Thr Tyr Ile His Trp Val Arg
145                 150                 155                 160

Gln Ala Pro Gly Lys Gly Leu Glu Trp Val Ala Arg Ile Tyr Pro Thr
                165                 170                 175

Asn Gly Tyr Thr Arg Tyr Ala Asp Ser Val Lys Gly Arg Phe Thr Ile
            180                 185                 190

Ser Ala Asp Thr Ser Lys Asn Thr Ala Tyr Leu Gln Met Asn Ser Leu
        195                 200                 205

Arg Ala Glu Asp Thr Ala Val Tyr Tyr Cys Ser Arg Trp Gly Gly Asp
    210                 215                 220

Gly Phe Tyr Ala Met Asp Tyr Trp Gly Gln Gly Thr Leu Val Thr Val
225                 230                 235                 240

Ser Ser
```